United States Patent [19]
Schneider et al.

[11] Patent Number: 5,466,356
[45] Date of Patent: Nov. 14, 1995

[54] POTENTIOSTAT CIRCUIT FOR ELECTROCHEMICAL CELLS

[75] Inventors: Alan A. Schneider, Wexford; Towner B. Scheffler, Bulter, both of Pa.

[73] Assignee: Mine Safety Appliances Company, Pittsburgh, Pa.

[21] Appl. No.: 235,379

[22] Filed: Apr. 29, 1994

[51] Int. Cl.$^6$ .......................... G01N 27/26; G01N 27/00
[52] U.S. Cl. .................. 204/406; 204/412; 204/431; 422/98
[58] Field of Search .................. 204/406, 412, 204/431, 432, 424; 422/98

[56] References Cited

U.S. PATENT DOCUMENTS 4,642,172   2/1987   Fruhwald ................. 204/412
5,100,530   3/1992   Dorr et al. ................. 204/406

Primary Examiner—Bruce F. Bell
Attorney, Agent, or Firm—James G. Uber

[57] ABSTRACT

A simple potentiostat circuit for use in biasing a three-electrode electrochemical cell is described wherein a direct electrical connection is made between the sensing electrode and the reference electrode during normal operation of the cell. Preferably the electrical connection is a resistor. By selecting the resistive value properly, the zero gas current of the cell is eliminated without negatively affecting the response of the cell.

8 Claims, 1 Drawing Sheet

POTENTIOSTAT CIRCUIT FOR ELECTROCHEMICAL CELLS

FIELD OF THE INVENTION

The present invention relates to potentiostat circuits for electrochemical cells used in gas monitors and particularly those three electrode electrochemical cells which require biasing to reduce the zero current.

BACKGROUND OF THE INVENTION

Potentiostat circuits are well known for biasing and controlling amperometric electrochemical cells. Such circuits are shown in FIG. 4 of U.S. Pat. No. 4,169,779, FIG. 4 of U.S. Pat. No. 4,171,253 and FIG. 3 of U.S. Pat. No. 4,326,927. These circuits are used in connection with a standard electrochemical cell or sensor which typically has three electrodes: (1) a sensing or working electrode; (2) a counter electrode; and (3) a reference electrode. The sensing electrode is used to detect the presence of the subject gas such as carbon monoxide (CO) or hydrogen sulfide ($H_2S$). The counter electrode and the reference electrode are usually connected to the potentiostat circuit which controls the operation of the electrochemical cell. There is, however, no direct electrical connection, and therefore essentially no current flows between the reference electrode and the sensing electrode.

U.S. Pat. No. 4,776,203 describes a potentiostat circuit wherein there is an electrical connection between the sensing electrode and the working electrode when the electrochemical cell is not operating. This connection, however, is eliminated when the electrochemical cell is operating. When the gas monitor containing the electrochemical cell is not being used, the sensing and reference electrodes are customarily connected together in a short circuit, or optionally via a resistor, in order to ensure that the monitor will produce reliable readings quickly after it has been started. If the sensing and reference electrodes are not initially connected, a large start-up current will be observed during initial operation. This patent teaches that it is necessary to break this electrical connection when the monitor is started up and while it is operational. The making and breaking of this connection is accomplished through a "Field Effect Trasistor (FET)" which has a very small resistance when it is turned off (effectively acting like a short circuit) and a very high resistance (effectively acting like an open circuit) when it is turned on. Thus, during operation, there is no direct electrical connection between the sensing electrode and the reference electrode.

From these references, it is clear that the sensing electrode of a three-electrode electrochemical cell used in a gas monitor can be controlled by a potentiostat circuit over a wide range of potentials. A special case exists for those gas monitors whose potentiostats are set to control the sensing electrode at substantially the same potential as the reference electrode, i.e., at a potential of essentially zero millivolts with respect to the reference electrode. Electrochemical cells which operate with a zero-millivolt potentiostat ideally require no current from the potentiostat circuit when the gas to be detected is absent. This occurs only if the potential of the sensing and reference electrodes are nearly identical when no current is drawn from the cell, i.e., when the rest potential is zero. Any deviation from this ideal case results in an undesirable zero-gas current when no gas is present. Although this current may be compensated for with an additional electronic compensation circuit, it would be simpler and less expensive if such compensation were not required.

It would be desirable therefore to have a potentiostat circuit which not only eliminated the start-up current but also significantly reduced the zero-gas current without having to make or break an electrical connection between the sensing electrode and the reference electrode.

SUMMARY OF THE INVENTION

Generally the present invention relates to an electrochemical cell comprising: a housing, a sensing electrode, a counter electrode and a reference electrode, wherein all three electrodes are contained within the housing, an electrolyte is contained within the housing and contacts each electrode, and a potentiostat circuit is connected to the electrodes, and further comprising a direct current path between the sensing electrode and the reference electrode during normal operation of the electrochemical cell. Preferably the direct current path is a resistor which can be looked at as a soft-short.

The present invention is particularly useful in electrochemical cells where the rest potential is small but not zero. The addition of a permanent direct current path between the sensing electrode and the reference electrode significantly reduces the zero gas current so that additional compensation circuitry is not required. The effect of this soft-short is to allow currents to flow between the sensing electrode and the reference electrode to reduce the potential difference between these two electrodes to less than a millivolt and preferably to less than 0.4 millivolts. All other circuitry in the potentiostat circuit remains the same.

Other details, objects and advantages of the present invention will become apparent as the following description of the presently preferred embodiments and presently preferred methods of practicing the invention proceed.

BRIEF DESCRIPTION OF THE DRAWING

In the accompanying drawing, a preferred embodiment and method of practicing the invention is illustrated in which.

DETAILED DESCRIPTION OF THE INVENTION

Figure 1:
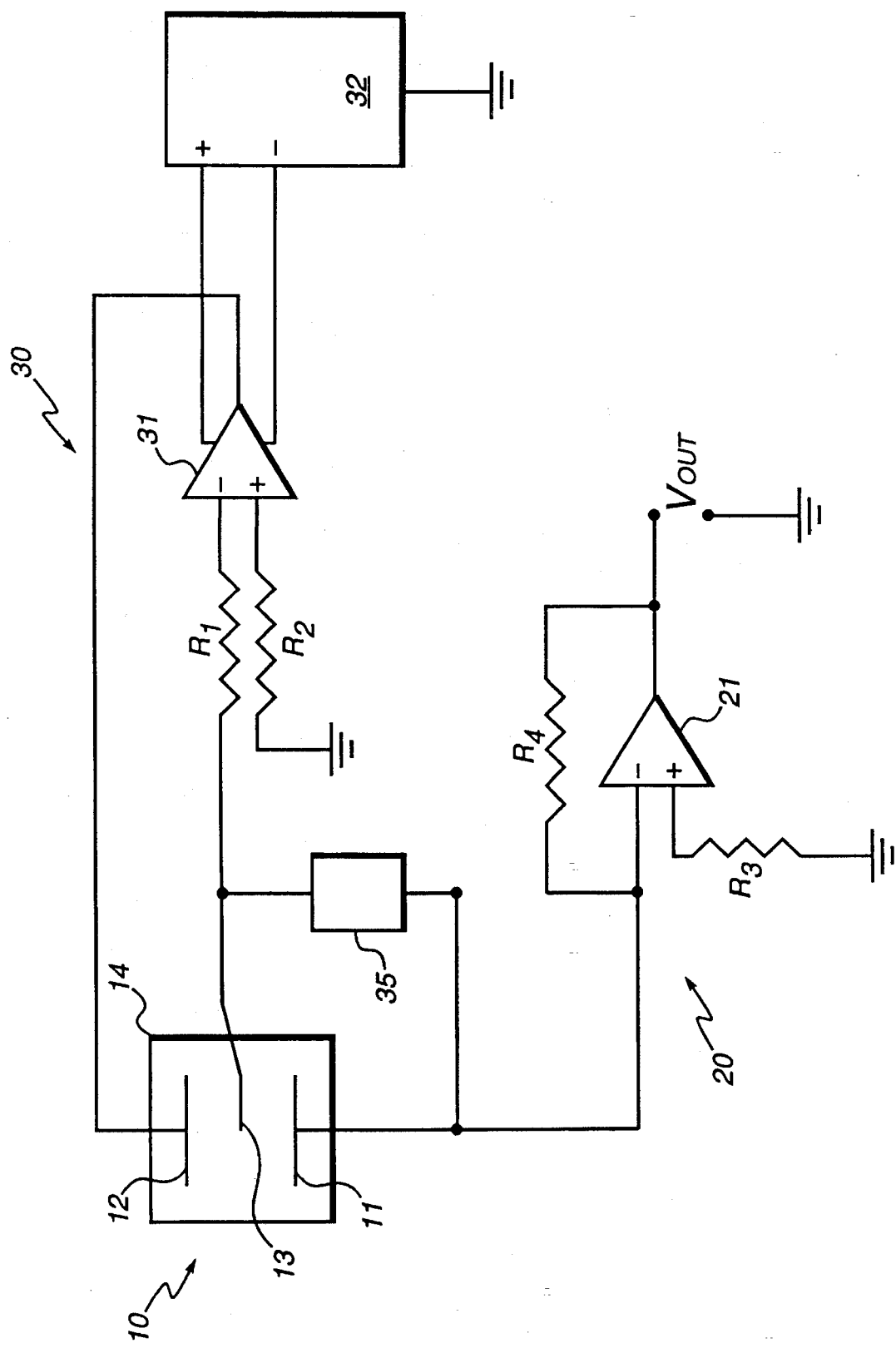
FIG. 1 is a schematic diagram of the potentiostat circuit of the present invention used with a three-electrode electrochemical cell.

A typical three-electrode electrochemical cell 10 such as is used for detecting CO or $H_2S$ is shown in FIG. 1. A sensing electrode 11, a counter electrode 12 and a reference electrode 13 are located within housing 14. An electrolyte is also contained within housing 14 and contacts all three electrodes. The reference electrode 13 is typically spaced between the counter electrode 12 and the sensing electrode 11. The sensing electrode 11 is also connected to an output circuit 20 while a potentiostat circuit 30 is connected between the counter electrode 12 and the reference electrode 13.

The output circuit 20 is preferably an amplifier circuit consisting of an op amp 21, resistor $R_3$ and resistor $R_4$. The output $V_{OUT}$ of the amplifier circuit 20 is directly related to the amount of the subject gas present at the sensing electrode 11.

The potentiostat circuit 30 also uses an op amp 31. Preferably the op amp 31 is driven by a power supply such as battery 32. This battery is also used to power op amp 21.

One input of the op amp 31 is connected to ground through $R_2$. The other input of the op amp is connected to the reference electrode through $R_1$. The output of op amp 31 is connected to counter electrode 12.

In a preferred embodiment, the electrical components shown in FIG. 1 have the following values: $R_1$=10 KΩ, $R_2$=10 KΩ, $R_3$=10 KΩ, and $R_4$=10 KΩ.

In the present invention, potentiostat circuit 30 further comprises a direct current path between reference electrode 13 and sensing electrode 11 during normal operation of the electrochemical cell 10. Preferably this direct electrical connection is permanent and is accomplished by circuit element 35. Preferably circuit element 35 is a resistor having a value of between 1 KΩ and 10 KΩ for an $H_2S$ or CO sensing cell having a sensing electrode area of about one square centimeter. In one preferred embodiment, circuit element 35 is a resistor having a value of 5 KΩ. Of course, for cells using a sensing electrode with a larger area, a proportionally smaller resistor would be needed.

Another advantage of the potentiostat circuit of the present invention is that it overcomes certain problems which can occur when the output of a potentiostat circuit is rectified. This can occur, for example, in a battery operated device where only a single voltage is available rather than both a positive and negative power source as is typically used to power an op amp. In this situation, only currents of one polarity are produced by the potentiostat circuit. If the zero current required by the cell is opposite to that of the current produced by the gas to be sensed, it is not possible to produce the appropriate zero current. As a result, the response time of the cell increases dramatically since the cell must see the gas to be sensed for a very long period before currents of the correct polarity are produced by the potentiostat circuit. This problem can be overcome by using a direct resistive connection between the sensing electrode 11 and the reference electrode 13.

Such a situation existed in a hydrogen sulfide cell made by "Mie Safety Appliances Company (MSA)" which had a surface area of about one square centimeter and used a single 2.8 V source. The offset in this cell between the sensing electrode and the working electrode was 34± 4 mV. This offset could not be compensated for by using a simple potentiostat circuit with a rectified output. When a potentiostat circuit of the present invention was used wherein the direct current path was a 5 KΩ resistor, the 34 mV offset decayed to near zero and the cell functioned properly during operation.

While presently preferred embodiments of practicing the invention have been shown and described with particularity in connection with the accompanying drawing, the invention may be otherwise embodied within the scope of the following claims.

What is claimed is:

1. In an electrochemical cell having a housing; a sensing electrode, a counter electrode and a reference electrode such that all three electrodes are contained within the housing; an electrolyte contained within the housing and contacting each electrode; and a potentiostat circuit connected to the reference and counter electrodes; the improvement comprising having a direct current path between the sensing electrode and the reference electrode during normal operation of the electrochemical cell.

2. The electrochemical cell as described in claim 1 wherein the direct current path is a resistor.

3. The electrochemical cell as described in claim 2 wherein the resistor has a value of between 1 KΩ and 10 KΩ.

4. The electrochemical cell as described in claim 3 wherein the resistor has a value of about 5 KΩ.

5. An electrochemical cell comprising:

a housing; a sensing electrode; a counter electrode; a reference electrode;

wherein all three electrodes are contained within the housing;

an electrolyte contained within the housing and contacting each electrode; and a potentiostat circuit connected to the electrodes and further comprising a permanent current path between the sensing electrode and the reference electrode.

6. The electrochemical cell as described in claim 5 wherein the permanent current path is a resistor.

7. The electrochemical cell as described in claim 6 wherein the resistor has a value of between 1 KΩ and 10 KΩ.

8. The electrochemical cell as described in claim 7 wherein the resistor has a value of about 5 KΩ.

* * * * *